United States Patent [19]

Synnatschke et al.

[11] 4,396,415
[45] Aug. 2, 1983

[54] HERBICIDE

[75] Inventors: Gotthard Synnatschke, Ludwigshafen; Walter Gueckel, Limburgerhof, both of Fed. Rep. of Germany

[73] Assignee: BASF Aktiengesellschaft, Fed. Rep. of Germany

[21] Appl. No.: 867,144

[22] Filed: Jan. 5, 1978

Related U.S. Application Data

[63] Continuation of Ser. No. 710,429, Aug. 2, 1976, abandoned.

[30] Foreign Application Priority Data

Oct. 27, 1975 [DE] Fed. Rep. of Germany ....... 2547968

[51] Int. Cl.$^3$ ............................................ A01N 43/58
[52] U.S. Cl. ..................................... 71/92; 71/DIG. 1
[58] Field of Search ............................. 71/92, DIG. 1

[56] References Cited

U.S. PATENT DOCUMENTS

| | | | |
|---|---|---|---|
| 2,213,477 | 9/1940 | Steindorff et al. | 71/DIG. 1 |
| 2,718,509 | 9/1955 | Lundsted et al. | 260/2 BP |
| 3,222,159 | 12/1965 | Reicheneder et al. | 71/92 |
| 3,737,551 | 6/1973 | Karsten et al. | 71/DIG. 1 |
| 3,914,122 | 10/1975 | Hyson | 71/DIG. 1 |
| 3,920,443 | 11/1975 | Drewe et al. | 71/94 |
| 3,948,636 | 4/1976 | Marks | 71/DIG. 1 |
| 4,021,226 | 5/1977 | Preugschas et al. | 71/92 |

FOREIGN PATENT DOCUMENTS

| | | | |
|---|---|---|---|
| 2412270 | 9/1975 | Fed. Rep. of Germany | 71/DIG. 1 |
| 813931 | 5/1959 | United Kingdom | 71/DIG. 1 |

OTHER PUBLICATIONS

McCutcheon, "Detergents & Emulsifiers", 1970 Ann. (1970) Alluved Pub. Co., p. 176.

*Primary Examiner*—Glennon H. Hollrah
*Attorney, Agent, or Firm*—Keil & Witherspoon

[57] ABSTRACT

Herbicide based on 1-phenyl-4-amino-5-chloro (or 5-bromo-)-pyridazone-(6) in the form of an aqueous suspension containing from 20 to 50 wt % of active ingredient, and silica and a block copolymer of propylene glycol, propylene oxide and ethylene oxide.

6 Claims, No Drawings

HERBICIDE

This is a continuation of application Ser. No. 710,429 filed Aug. 2, 1976, now abandoned.

The present invention relates to a herbicide based on 1-phenyl-4-amino-5-chloro(or 5-bromo-)-pyridazone-(6) in the form of an aqueous suspension.

It is known to use pyridazones, especially those mentioned above, as herbicides. The active ingredient is usually employed in the form of a liquor which is sprayed on to the plants. It is known to produce this spray liquor from water and a spray powder or a highly concentrated aqueous suspension.

The disadvantage of the spray powder is that the herbicidal action, especially in a dry climate, is slow to set in and is often unsatisfactory. These drawbacks are caused by poor quality spray liquor, non-uniform trituration of the product, uneven distribution of the herbicide on plants and soil, and poor penetration of the leaves of unwanted plants, which are less permeable after a long period of dry weather.

These disadvantages of the spray powder are in part overcome by prior art highly concentrated aqueous suspensions (German Laid-Open Application DOS 2,412,270; U.S. Pat. No. 3,834,889, Example 6e). However, even these formulation forms have a decisive disadvantage—as two-phase systems (solid-liquid) they are unstable and tend to separate; the longer the preparation is stored and the higher the storage temperature is, the more marked is the degree of separation. In many cases extremely viscous, compact deposits form which cannot be redispersed by simple shaking. When producing an aqueous suspension in accordance with Example 6e of U.S. Pat. No. 3,834,889 a very thixotropic paste is obtained which immediately firms and is therefore difficult to remove completely from a vessel when it is to be diluted with water to produce a spray liquor.

We have now found that these disadvantages manifested by highly concentrated aqueous suspensions do not occur when they contain silica and a block copolymer of propylene glycol, propylene oxide and ethylene oxide.

For example, herbicide suspensions according to the invention contain 20 to 50 wt% of active ingredient
5 to 15 wt% of antifreeze
2 to 10 wt% of dispersant
0.5 to 5 wt% of silica
0.5 to 5 wt% of block copolymer
and water makeup.

Examples of antifreeze are ethylene glycol, propylene glycol, glycerol, and urea; ethylene glycol is preferred.

By dispersants are meant all surfactants known as auxiliaries in the formulation of plant protection agents; it is preferred to use the sodium salt of a condensate product of phenolsulfonic acid, urea and formaldehyde. Such condensation products are described for example in German Pat. Nos. 1,113,457 and 1,178,081.

It is preferred to use the silica in artificial form.

By block copolymer is meant a product formed by reacting propylene glycol first with propylene oxide and then with ethylene oxide. It is preferred to use a product having a polypropylene oxide backbone of molecular weight 3,000 to 3,500 and containing 50% of ethylene oxide units, so that the total molecular weight is about 6,000 to 7,000.

The water is preferably fully demineralized.

The herbicides according to the invention are prepared by finely grinding the suspended active ingredients, together with the other components, in mills (e.g., sand or Perl mills). After trituration at least 80 wt% of the particles are less than $2\mu$.

The herbicides according to the invention have the same good herbicidal action as the prior art spray powders and concentrated aqueous suspensions.

The following examples illustrate the advantageous properties of the herbicides of the invention.

EXAMPLE 1

43 parts by weight of 1-phenyl-4-amino-5-chloropyridazone-(6), 10 parts by weight of ethylene glycol, 6 parts of a sodium salt of a condensation product of phenolsulfonic acid, urea and formaldehyde, 2 parts of artificial silica, and 3 parts of a block copolymer consisting of a polypropylene oxide backbone having a molecular weight of about 3,250 on to which ethylene oxide has been grafted up to a molecular weight of about 6,500, are mixed and made up to 100 ml with water (sample B, according to the invention).

43 parts by weight of 1-phenyl-4-amino-5-chloropyridazone-(6), 2 parts of the diethanolamine salt of dodecylbenzenesulfonic acid, 4 parts of a sodium salt of a condensation product of sulfonated naphthalene with urea and formaldehyde are mixed and made up to 100 ml with water (sample A = Example 1 of German Laid-Open Application DOS No. 2,412,270).

Both mixtures were ground for the same length of time in a Perl mill, the resultant particle size distribution of the two samples being the same. In this particular instance approximately 95% of the particles were smaller than $2\mu$.

Both samples were stored under identical conditions at 20°, 30° and 40° C.

Upon commencement of storage, sample A was a thixotropic paste which was easy to make flowable by shaking. After storage for 6 months at the said temperatures, the properties had changed as follows:

20° C.: thick paste which was difficult to make flowable even by prolonged shaking;

30° and 40° C.: firm paste which prolonged and vigorous shaking was unable to make flowable.

Sample B was, upon commencement of storage, a thin paste which had good flow properties without being shaken. After 6 months' storage at the said temperatures the properties of the sample had not changed except for the formation of a thin layer of clear supernatant liquid. This slight inhomogeneity can be eliminated by brief shaking. What is important is that the sample retains its good flow properties, and that the quality of the product does not depend on the temperature at which it is stored.

Whereas sample A was, after 6 months' storage at 20° C., practically incapable of being used for producing a spray liquor, sample B, after the same storage period at 40° C., was just as ready for use as it was immediately after having been manufactured. Particularly this result at elevated temperatures implies a storage stability of several years at normal temperatures (20° C. and less).

EXAMPLE 2

43 parts by weight of 1-phenyl-4-amino-5-chloropyridazone-(6), 5 parts by weight of a condensation product of sulfonated phenol, urea and formaldehyde, which product has been condensed with a separately prepared phenol/formaldehyde condensate, 10 parts of ethylene glycol, and 0.1 part of triisobutyl phosphate are mixed, and made up to 100 ml with water (sample C, approximates to sample B, but without block copolymer and silica).

This mixture is ground as described in Example 1 and stored at various temperatures in comparison to sample B (Example 1).

Upon commencement of storage, sample C was a viscous paste which still had adequate flowability. After 6 months' storage at 20°, 30° and 40° C. this property had not changed, except for the formation of a thin layer of clear liquid above the paste. The incipient homogeneity of the sample was able to be restored by vigorous shaking. However, after storage at 50° C. for 6 months the sample was unserviceable as it had separated out into a considerable amount of clear supernatant liquid and a thick and extremely viscous deposit which was not able to be made flowable by stirring.

The properties of sample B (according to the invention) are described in Example 1. At the storage temperature of 50° C. additionally used in Example 2 its properties are still the same as after storage at 40° C.—it can be made homogeneous and ready for use by slight shaking.

This example demonstrates the superiority of the sample according to the invention at high storage temperatures.

EXAMPLE 3

The following samples were prepared:
(a) in accordance with Example 1, sample B;
(b) in accordance with Example 1, sample B, but without the 2 parts of artificial silica (sample D).

Both samples were stored under the same conditions. Immediately after manufacture there was no difference between samples B and D. However, after as little as 4 weeks' storage at 20°, 30°, 40° and 50° C., sample D was unserviceable: in all the specimens a viscous deposit had formed (independent of temperature) which stuck to the bottom of the vessel and was unable to be redispersed by prolonged and vigorous shaking. Sample B remained unchanged during this storage period.

EXAMPLE 4

To compare sample A (I) with sample B (II), 4 tests were carried out in the open at different localities. The soil was in each case a sandy loam. The active ingredients were applied at a rate of 2.6 kg per hectare. The diluent for spraying was water. Application was effected before emergence of the crop and unwanted plants, and on some plots after emergence of the plants as well. In the latter case, the sugar beet plants were in the first to second genuine leaf stage, and the weeds had from one to five genuine leaves. All the experiments were replicated 4 times. Sugar beet plants were not grown on every plot, and the weeds varied and were not represented everywhere. Some species occurred once, others 3 times.

The following table contains the values assessed visually 2 to 4 weeks after the postemergence application.

TABLE

Results
1. Sample A and sample B caused, when applied both pre- and postemergence, very little or no damage to the sugar beet.
2. When applied preemergence, both samples had on average a good action on unwanted plants. Some species were poorly controlled, and many very well controlled.

TABLE-continued
3. When applied postemergence, the action of both samples was, under the actual test conditions, not quite adequate; sample B was slightly superior.
4. Both samples can be deemed equivalent with regard to crop plant tolerance and weed control.

Comparison of two samples for weed control in sugar beet after preemergence ("pre") and postemergence ("post") application

| | Formulations and biological action (% damage - visual assessment) | | | |
|---|---|---|---|---|
| | Sample A 2.6 kg/ha | | Sample B 2.6 kg/ha | |
| | Application | | | |
| Test plants | pre | post | pre | post |
| Beta vulgaris (sugar beet) | 1.0 | 0 | 1.0 | 1.5 |
| Poa annua | 100 | 97.5 | 100 | 98 |
| Atriplex patula | 85 | 32.5 | 85 | 60 |
| Brassica napus var. napobrassica | 95 | 90 | 95 | 91 |
| Chenopodium album | 87 | 68 | 84 | 75 |
| Galium aparine | 70 | 49 | 70 | 60 |
| Lamium purpureum | 99 | 91 | 98 | 94 |
| Matricaria chamomilla | 98 | 81 | 99 | 89 |
| Polygonum aviculare | 91 | 20 | 93 | 65 |
| Polygonum convolvulus | 95 | 79 | 95 | 88 |
| Raphanus raphanistrum | 97 | 32.5 | 93 | 32.5 |
| Sinapis arvensis | 75 | 75 | 75 | 75 |
| Stellaria media | 95 | 65 | 95 | 86 |
| Thlaspi arvense | 97.5 | 100 | 97.5 | 99 |
| Veronica persica | 100 | 89 | 99 | 95 |
| Vicia spp. | 97 | 25 | 95 | 32.5 |
| Viola tricolor | 97.5 | 49 | 98 | 32.5 |
| Average for all weeds | 93 | 65 | 92 | 71 |

Scale 0 to 100%
0 = no damage
100 = all plants destroyed or did not emerge

We claim:
1. A herbicidal composition in the form of an aqueous suspension, comprising:
from 20 to 50% of 1-phenyl-4-amino-5-chloropyridazone-(6) or 1-phenyl-4-amino-5-bromopyridazone-(6) as active ingredient,
from 2 to 10 wt% of dispersant consisting essentially of condensate product of a phenolsulfonic acid, urea and formaldehyde and water, and
from 0.5 to 5%, respectively, of (a) silica and (b) a block copolymer of propylene glycol, propylene oxide and ethylene oxide, wherein said block copolymer is formed by reacting propylene glycol with propylene oxide to form a propylene oxide backbone and then reacting said propylene oxide backbone with ethylene oxide such that the molecular weight of the resulting block copolymer is about 6,000 to 7,000.

2. A herbicidal composition in the form of an aqueous suspension, consisting essentially of:
from 20 to 50% of 1-phenyl-4-amino-5-chloropyridazone-(6) or 1-phenyl-4-amino-5-bromopyridazone-(6) as active ingredient,
from 2 to 10 wt% of dispersant consisting of the sodium salt of a condensate product of phenolsulfonic acid, urea and formaldehyde, and water, and
from 0.5 to 5%, respectively, of (a) silica and (b) a block copolymer of propylene glycol, propylene oxide and ethylene oxide, wherein said block copolymer is formed by reacting propylene glycol with propylene oxide to form a propylene oxide backbone and then reacting said propylene oxide backbone with ethylene oxide such that the block copolymer has a polypropylene oxide backbone of molecular weight 3,000 to 3,500 and contains about 50% by ethylene oxide units.

3. A herbicidal composition as set forth in claim 1, wherein the silica is in artificial form.

4. A herbicidal composition as set forth in claim 1, which also contains from 5 to 15 wt% of antifreeze.

5. A herbicidal composition as set forth in claim 1, wherein said dispersant is the sodium salt of a condensation product of phenol-sulfonic acid, urea and formaldehyde.

6. A process for controlling the growth of unwanted plants which comprises treating the plants or soil with an effective amount of a herbicidal composition according to claim 1.

* * * * *